US00PP37638P2

(12) United States Plant Patent
O'Connell

(10) Patent No.: US PP37,638 P2
(45) Date of Patent: Aug. 18, 2026

(54) ***PORTULACARIA* 'Sunkissed'**

(50) Latin Name: *Portulacaria afra*
Varietal Denomination: Sunkissed

(71) Applicant: Altman Specialty Plants llc, Vista, CA (US)

(72) Inventor: Renee O'Connell, Pala, CA (US)

(73) Assignee: Altman Specialty Plants llc, Vista, CA (US)

( * ) Notice: Subject to any disclaimer, the term of this patent is extended or adjusted under 35 U.S.C. 154(b) by 0 days.

(21) Appl. No.: 19/264,395

(22) Filed: Jul. 9, 2025

(51) Int. Cl.
*A01H 5/12* (2018.01)
*A01H 6/00* (2018.01)

(52) U.S. Cl.
USPC ..... Plt./373
CPC ..... *A01H 6/00* (2018.05); *A01H 5/12* (2013.01)

(58) Field of Classification Search
USPC ..... Plt./226, 373
See application file for complete search history.

*Primary Examiner* — Susan Mccormick Ewoldt
*Assistant Examiner* — Zachariah Allan Kay

(57) ABSTRACT

A new and distinct cultivar of *Portulacaria afra* plant named 'SUNKISSED' is disclosed, characterized by long, gracefully cascading reddish branches of small green and creamy yellow variegated leaves. Plants offset at an early age, resulting in a much-branched morphology as a smaller plant. The new cultivar is a *Portulacaria afra*, typically produced as a container plant, particularly adapted for hanging basket creations as well as accents in patio plantings.

1 Drawing Sheet

Latin name of the genus and species: *Portulacaria afra*.
Cultivar denomination: 'SUNKISSED'.

BACKGROUND OF THE INVENTION

The new cultivar is a product of a naturally occurring whole plant mutation in a commercial nursery in Vista, California. The parent is the unpatented commercial variety *Portulacaria afra* prostrate form (non-variegated). *Portulacaria afra* 'Sunkissed' was found and selected by the inventor among several pots of the parent variety at a commercial greenhouse in Vista, California during March of 2021.

Asexual reproduction of the new cultivar 'SUNKISSED' was first performed by vegetative tip cuttings at a commercial greenhouse in Vista, California in August of 2021. 'SUNKISSED' has since produced at least 15 generations and has shown that the unique features of this cultivar are stable and reproduced true to type.

SUMMARY OF THE INVENTION

The cultivar 'SUNKISSED' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SUNKISSED'. These characteristics in combination distinguish 'SUNKISSED' as a new and distinct *Portulacaria* cultivar:

1. The new cultivar *Portulacaria afra* 'Sunkissed' forms long, gracefully cascading reddish branches of small green and creamy yellow variegated leaves.
2. Due to the cascading morphology of *Portulacaria afra* 'Sunkissed', this plant is particularly adapted for hanging basket creations as well as accents in patio plantings.

3. *Portulacaria afra* 'Sunkissed' begins to offset at an early age; resulting in a much-branched morphology as a smaller plant. For this reason, and because of the more diminutive morphology, the cultivar *Portulacaria afra* 'Sunkissed' can be utilized in a multitude of pot sizes, including smaller pot sizes.
4. *Portulacaria afra* 'Sunkissed', can be induced to attain a beautiful pink blush when exposed to cool, bright conditions in the winter.
5. As *Portulacaria afra* 'Sunkissed' offsets heavily at a younger age, the result is the enhancement of propagation in a commercial nursery environment.

PARENTAL COMPARISON

Plants of the new cultivar 'SUNKISSED' are similar to the parent in most horticultural characteristics. However, plants of the new cultivar differ from the parent in the following:

1. *Portulacaria afra* 'Sunkissed' is a variegate, whereas the parent variety, *Portulacaria afra* (prostrate form) is not.
2. *Portulacaria afra* 'Sunkissed' has a more compact morphology than the parent plant *Portulacaria afra* (prostrate form).

COMMERCIAL COMPARISONS

'SUNKISSED' can be compared to the unpatented commercial cultivar *Portulacaria afra* 'Manny', U.S. Plant Pat. No. 32,213. The two *Portulacaria* varieties are similar in most horticultural characteristics; however, the new cultivar differs in the following:

1. *Portulacaria afra* 'Sunkissed' displays a more diminutive morphology than does *Portulacaria afra* 'Manny'
2. *Portulacaria afra* 'Sunkissed' displays similar chunky, thickened leaves, as does *Portulacaria afra* 'Manny'.

3. *Portulacaria afra* 'Sunkissed' displays a more cascading morphology, suitable for a hanging basket, whereas *Portulacaria afra* 'Manny' is a more upright plant.

'SUNKISSED' can be compared to the unpatented commercial cultivar *Portulacaria afra* 'Lilliput', U.S. Plant Pat. No. 32,011. The two *Portulacaria* varieties are similar in most horticultural characteristics; however, the new cultivar differs in the following:

1. *Portulacaria afra* 'Sunkissed' exhibits variegated leaves, whereas the leaves of *Portulacaria afra* 'Lilliput' are solid green, without variegation.
2. *Portulacaria afra* 'Sunkissed' exhibits chunky, thickened leaves, whereas *Portulacaria afra* 'Lilliput' does not display thickened leaves.
3. *Portulacaria afra* 'Sunkissed' displays a graceful cascading morphology, ideal for hanging baskets, whereas *Portulacaria afra* 'Lilliput' exhibits a more upright morphology.

BRIEF DESCRIPTION OF THE PHOTOGRAPH

The photograph was taken using conventional techniques and equipment. While the colors in the photograph may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of new *Portulacaria afra* 'SUNKISSED'. The included figure is a photograph of a typical plant of 'SUNKISSED' in a 6-inch pot at 5 months of age from a rooted cutting. The plant was grown in a greenhouse in Vista, CA. (approximately 2500 foot candles). Temperatures ranged from approximately 34 F to 90 F.

DETAILED BOTANICAL DESCRIPTION

In the following description, color references are made to The Royal Horticultural Society Color Chart, 2015 edition, except where general terms of ordinary dictionary significance are used. The following observations and measurements describe 'SUNKISSED' plants in a commercial shadehouse in Vista, California. Temperatures ranged from 34° F. to 90° F. during the night and day. No artificial light, photoperiodic treatments or chemical treatments were given to the plants. Natural light conditions were approximately 2500 foot candles of light. Measurements and numerical values represent averages of typical plant types.

Botanical classification: *Portulacaria afra* 'SUNKISSED'.

Age of the plant described: About 5 months.

PROPAGATION

Time to initiate roots: Approximately 25 days at 22° C.

Propagation method: Vegetative tip cuttings.

PLANT

Growth habit: Tender succulent. Cascading.

Container size: 6-inch.

Height: Approximately 5 to 8 cm.

Plant spread: Approximately 32 cm, in a 6-inch pot.

Quantity branches: 4 to 6 main basal branches. Main branches have on average 8 lateral branches.

Branch description:

*Length*.—Average range 10 to 15 cm.

*Diameter*.—Approximately 5 mm.

*Texture*.—Glabrous.

*Shape*.—Round.

*Color*.—Immature: RHS Greyed-Purple 187A. Mature: RHS Greyed-Green 194C.

Root description: Densely fibrous. RHS Grey-Brown N199A and N199B.

FOLIAGE

Leaf:

*Arrangement*.—Opposite.

*Average length*.—Average range 1.4 to 2 cm.

*Average width*.—1.0 to 1.4 cm.

*Shape of blade*.—Broad obovate.

*Apex*.—Broad rounded, and frequently mucronate.

*Base*.—Broad taper.

*Margin*.—Entire.

*Texture of top surface*.—Glabrous.

*Texture of bottom surface*.—Glabrous.

*Appearance of top surface*.—Slightly glossy.

*Appearance of lower surface*.—Matte.

*Quantity of leaves per branch*.—Approximately 30 to 50.

*Leaf internode*.—4 mm.

*Color*.— Young foliage upper side: Center strip RHS Green (About 143C fading out to 138B. Large marginal coloration Yellow-Green 150D. Green section covers 10 to 30% of leaf, the rest is the lighter Yellow-Green color. Young foliage, under side: Center strip RHS Green 143C fading out to 138B. Large marginal coloration Yellow-Green 149D. Green section covers 10 to 30% of leaf, the rest is the lighter Yellow-Green color. Mature foliage upper side: Center section RHS Green 139C. Streaks surrounding center section 139D. Large marginal coloration Yellow 4D. Green section covers 70 to 80% of leaf, the rest is the lighter Yellow color. Mature foliage, under side: Center section RHS Green 139C. Streaks surrounding center section 139D. Large marginal coloration Yellow 4D. Green section covers 70 to 80% of leaf, the rest is the lighter Yellow color.

*Venation*.—There is no visual appearance of venation.

FLOWER

Flowering not observed.

OTHER CHARACTERISTICS

Fruits and seeds: Not observed to date.

Temperature tolerance: USDA zones 10 and above.

Disease/pest resistance: Neither resistance nor susceptibility to standard pathogens or pests of *Portulacaria* observed.

Drought tolerance: Good tolerance for drought. Supplemental water is not necessary after plants are well established in the ground. Plants in containers can dry out completely for more than a week without damage to the plant.

What is claimed is:

1. A new and distinct cultivar of *Portulacaria afra* plant named 'SUNKISSED' as herein illustrated and described.

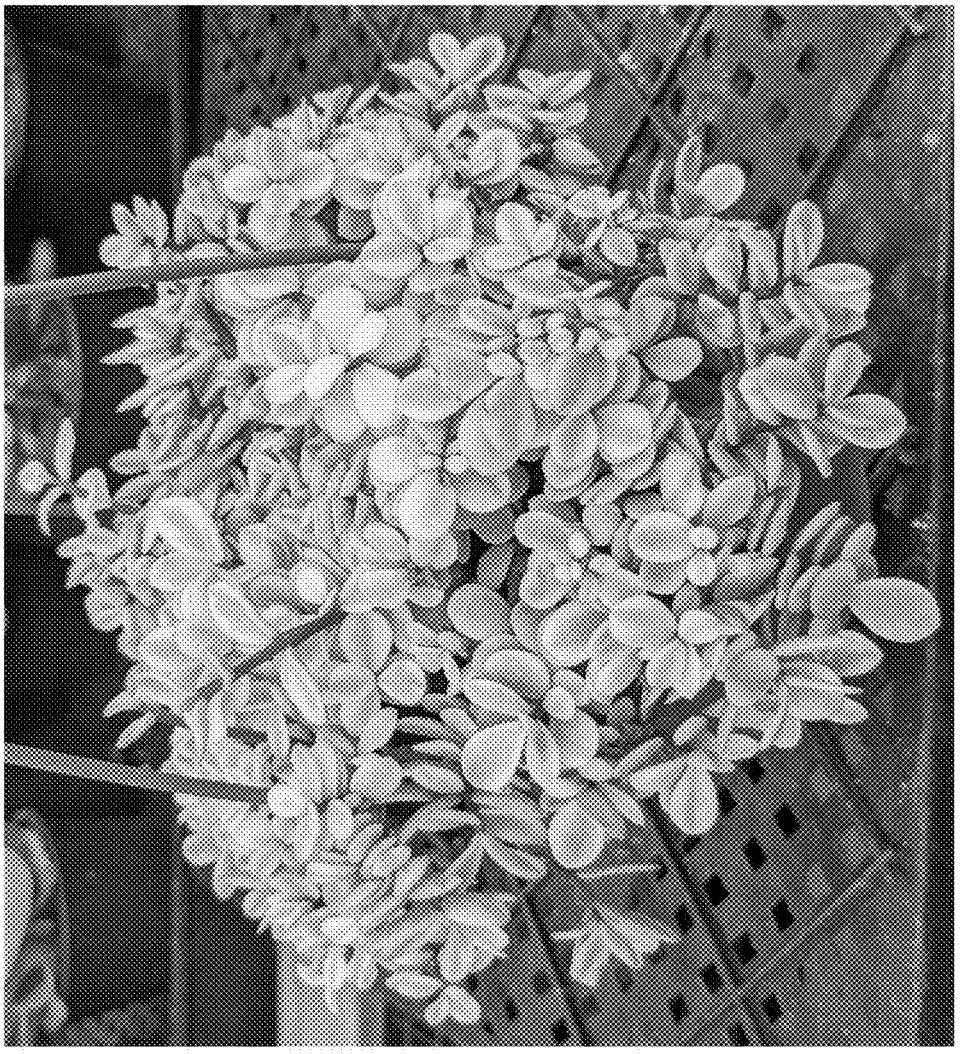

* * * * *